US00PP20998P2

(12) United States Plant Patent
Ichie

(10) Patent No.: US PP20,998 P2
(45) Date of Patent: May 18, 2010

(54) ***HYDRANGEA* PLANT NAMED 'KOMPEITO'**
(50) Latin Name: *Hydrangea macrophylla*
Varietal Denomination: Kompeito

(76) Inventor: Toyokazu Ichie, 3-46 Hongou, Kakegawa-city, Shizuoka (JP) 436-0111

( * ) Notice: Subject to any disclaimer, the term of this patent is extended or adjusted under 35 U.S.C. 154(b) by 0 days.

(21) Appl. No.: 12/383,618

(22) Filed: Mar. 28, 2009

(51) Int. Cl.
*A01H 5/00* (2006.01)

(52) U.S. Cl. ..... Plt./250

(58) Field of Classification Search ..... Plt./250
See application file for complete search history.

*Primary Examiner*—Kent L Bell
(74) *Attorney, Agent, or Firm*—Penny J. Aguirre

(57) ABSTRACT

A new cultivar of *Hydrangea macrophylla* named 'Kompeito' that is characterized by its re-blooming habit with inflorescences produced from early summer until fall with removal of spent blooms, its consistently well formed, large sized, lacecap type inflorescences with a mass of fertile flowers surrounded by large double flowers on long petioles and smaller double flowers with sepals having white margins and centers that are blue to pink in color depending on soil acidity and aluminum uptake, its compact growth habit, and its hardiness at least in U.S.D.A. Zones 5 to 9.

2 Drawing Sheets

Botanical classification: *Hydrangea macrophylla.*
Varietal denomination: 'Kompeito'.

BACKGROUND OF THE INVENTION

The present invention relates to a new and distinct cultivar of *Hydrangea macrophylla* and will be referred to hereafter by its cultivar name, 'Kompeito'. 'Kompeito' represents a new bigleaf *hydrangea*, a deciduous shrub grown for landscape use and for use as a potted plant.

'Kompeito' was derived from an ongoing controlled breeding program that focuses on developing new cultivars of *Hydrangea* for landscape and container use. 'Kompeito' originated from a cross made in the Inventor's nursery in June 1999 in Shizuoka, Japan between two unpatented proprietary selections of *Hydrangea macrophylla*; the female parent designated as H3-133 and the male parent designated as H1-101. The new *Hydrangea* was selected as a unique single plant from the progeny of the cross in February 2006.

Asexual reproduction of the new cultivar was first accomplished by the Inventor using softwood stem cuttings in Shizuoka, Japan in May 2007. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Kompeito' as a unique cultivar of *Hydrangea macrophylla.*

1. 'Kompeito' exhibits a re-blooming habit with inflorescences produced from early summer until fall with removal of spent blooms.
2. 'Kompeito' has consistently well formed, large sized, lacecap type inflorescences with large double sterile flowers surrounding a mass of fertile flowers and some smaller double sterile flowers.
3. 'Kompeito' exhibits sterile flowers with sepals having white margins and centers that are blue to pink in color depending on soil acidity and aluminum uptake.
4. 'Kompeito' exhibits a compact plant habit.
5. 'Kompeito' is hardy at least to U.S.D.A. Zones 5 to 9.

'Kompeito' differs from its female parent, H3-133, in having double sterile flowers whereas H3-133 exhibits single sterile flowers. 'Kompeito' differs from its male parent, H1-101, in having sterile flowers with sepals that have white margins, whereas H1-101 exhibits sterile flowers with sepals that are uniformly light purple in color and lack white margins.

'Kompeito' can also be compared to 'Jogasaki' (not patented), a cultivar with similar inflorescence form and color, however the sepals of the sterile flowers of 'Jogasaki' lack white margins.

BRIEF DESCRIPTION OF THE DRAWINGS

The accompanying color photographs illustrate the overall appearance and distinct characteristics of the new *Hydrangea.*

The photograph in FIG. 1 was taken of a three year-old plant of 'Kompeito' as grown outdoors in a three-gallon container in Shizuoka, Japan and illustrates the foliage coloration and inflorescence coloration when grown under acidic soil conditions with sufficient aluminum uptake.

Figure 1:
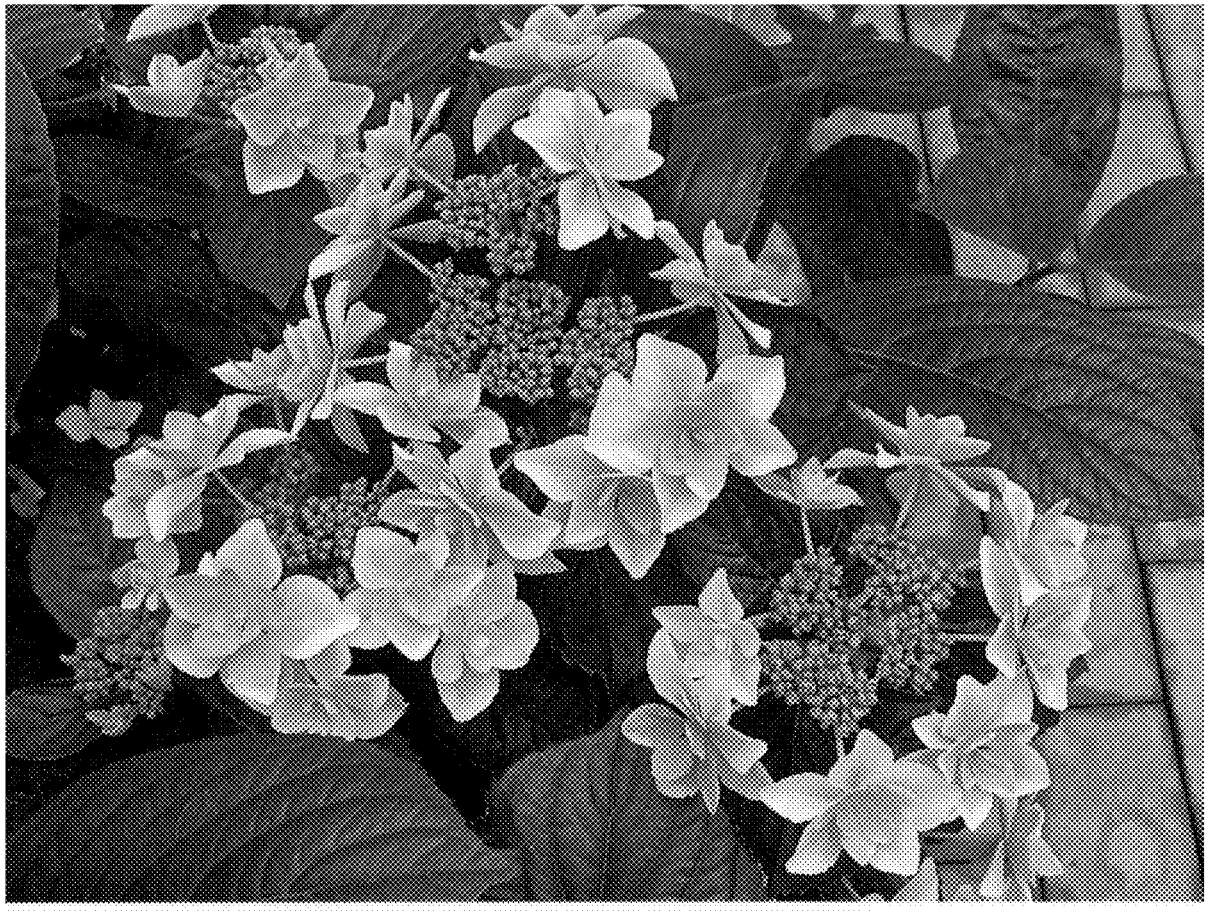
Figure 2:
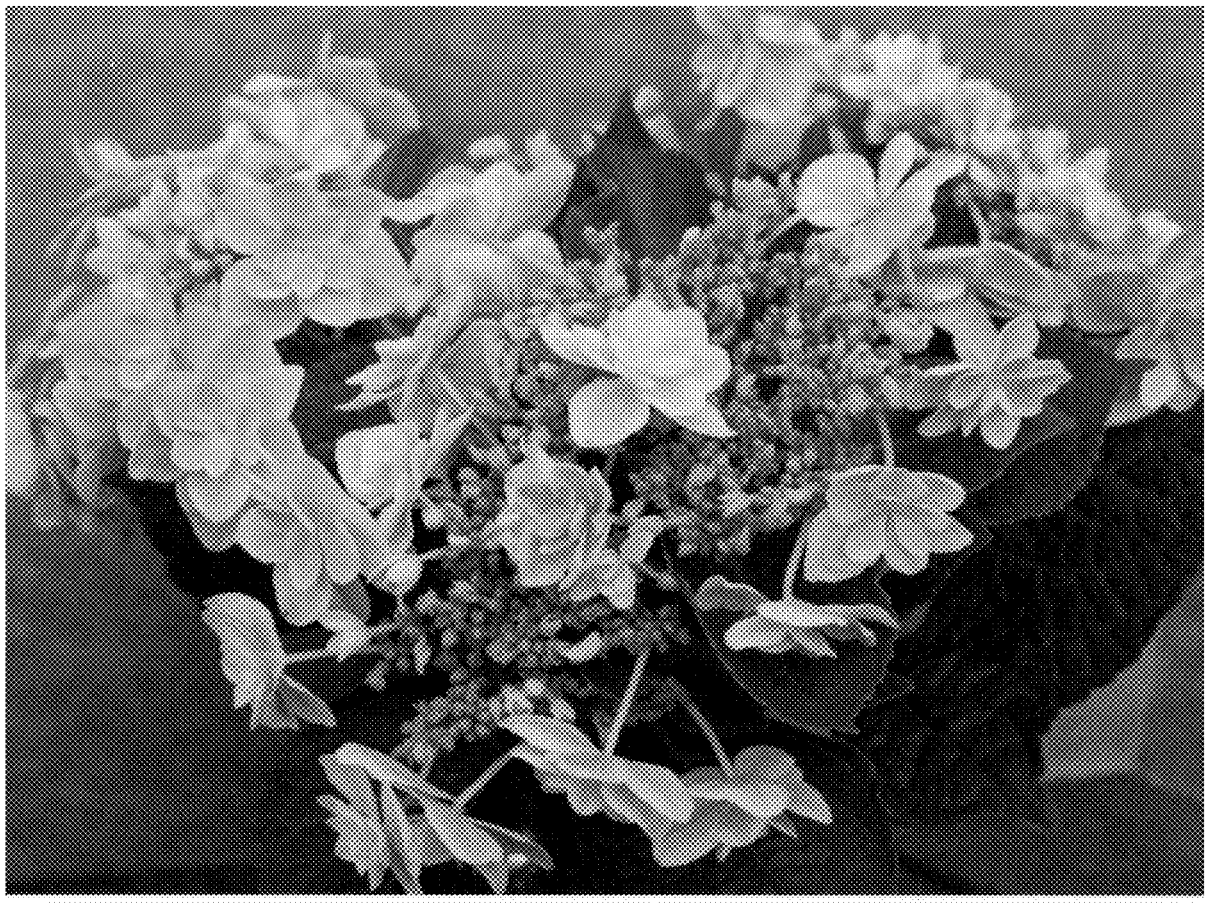

The photograph in FIG. 2 was taken of stems taken from a three year-old plant of 'Kompeito' as grown outdoors in three-gallon container in Shizuoka, Japan and illustrates the inflorescence coloration when grown under alkaline soil conditions. The colors in the photographs may differ slightly from the color values cited in the detailed botanical description, which accurately describe the colors of the new *Hydrangea.*

BOTANICAL DESCRIPTION OF THE PLANT

The following is a detailed description of a three year-old plants of 'Kompeito' as grown outdoors in three-gallon container in Shizuoka, Japan. The detailed sterile sepal color data was taken from plants growing both under acidic conditions and alkaline conditions where differences exist. Phenotypic differences may be observed with variations in environmental, climatic, and cultural conditions. The color determination is in accordance with the 2007 R.H.S. Colour Chart of The Royal Horticultural Society, London, England, except where general color terms of ordinary dictionary significance are used.

General description:

*Blooming period.*—Reblooming from June until frost from with removal of spent blooms in Shizuoka, Japan.

*Plant habit.*—Broadly upright, compact, deciduous shrub.

*Height and spread.*—Reaches about 60 cm in height and width on three-year-old plants in a 3-gallon container.

*Hardiness.*—At least to U.S.D.A. Zones 5 to 9.

*Diseases resistance.*—No susceptibility or resistance to diseases known to effect *H. macrophylla* has been observed.

*Root description.*—Fibrous.

Growth and propagation:

*Propagation.*—Softwood stem cuttings.

*Growth rate and vigor.*—Moderate.

Stem description:

*Stem shape.*—Round, solid.

*Stem strength.*—Strong.

*Stem color.*—New growth; 144A with lenticels 200A, bark; N199B to 199C.

*Stem size.*—An average of 20 cm (to base of inflorescence), average of 7 mm in width.

*Stem surface.*—Glabrous, satiny and very sparsely covered with long lenticels; about 2 per square cm and an average of 3.5 mm in length and 0.7 mm diameter, stem becomes bark-like with age.

*Branching.*—A single dormant stem will produce an average of 4 lateral branches, sublateral branching is determined by pinching; 2 stems develop per pinched node.

Foliage description:

*Leaf shape.*—Elliptic to broadly elliptic.

*Leaf arrangement.*—Opposite.

*Leaf division.*—Simple.

*Leaf number.*—Average of 12 (6 pairs) per lateral branch 17 cm in length.

*Leaf base.*—Cuneate.

*Leaf apex.*—Cuspidate.

*Leaf margins.*—Crenated with tiny point at each apex, average of 17 per side on a mature leaf 17 cm in length.

*Leaf venation.*—Pinnate, recessed on upper surface, color 145B to 145C on upper surface and 145C to 147D on lower surface.

*Leaf size.*—Up to 17 cm in length and 12.5 cm in width.

*Leaf attachment.*—Petiolate.

*Leaf surface.*—Glabrous and satiny on upper surface, glabrous and finely puberulent on lower surface.

*Leaf color.*—Upper surface; between 147A and N137A, lower surface; 138B with puberulent coating of 147D.

*Petioles.*—Average of 1.8 cm in length and 5 mm in width, 144A to 144B in color, glabrous surface, sulcate on upper surface.

Inflorescence description:

*Inflorescence type.*—Terminal compound corymb, lacecap type, comprised of a mass of fertile (pistillate) flowers in the center and larger double sterile flowers on long nodding pedicels surrounding the border with some smaller double sterile flowers emerging from pistillate flowers.

*Lastingness of inflorescence.*—Persistent but color is retained for about 4 weeks.

*Inflorescence number.*—One per lateral or sublateral stem if pinched.

*Inflorescence size.*—Average of 9 cm in depth and 20 cm in diameter when fully open.

*Flower number.*—Average of 8 double sterile flowers on perimeter, average of 200 small pistillate flowers.

*Flower fragrance.*—None.

*Flower form.*—Large double flowers are rotate and spreading, small double flowers are open campanulate to spreading and pistillate flowers are campanulate.

*Inflorescence aspect.*—Flattened globose in shape with nodding flowers on perimeter.

*Flower size.*—Smaller double flowers; average of 1.8 cm in diameter and 4 mm in depth, larger double flowers; average of 4.5 cm in diameter and 1 cm in depth, pistillate flowers; average of 4 mm in diameter and 5 cm in depth.

*Flower buds.*—Large double flowers; average of 1 cm in length and 4 mm in width, oval in shape, 145C in color, smaller double flowers; average of 4 cm in length and 3 mm in width, oval in shape, 145C in color in color, pistillate flowers; average of 2 mm in width and diameter, globose in shape, 145A in color.

*Peduncles.*—Strong, average of 1.8 cm in length to base of corymb and 3 mm in width, 147C in color, covered with very short hairs.

*Pedicels.*—Sterile flowers; average of 2.8 cm in length and 2 mm in width, 75C in color, hairy surface, small double flowers; average of 6 mm in length and 2 mm in width, NN155B to 75D in color, hairy surface, pistillate flowers; average of 2 mm in length and 1 mm in width, and 145D in color, hairy surface.

*Petals.*—4, present on pistillate flowers only, rotate in arrangement, elliptic in shape, entire margin, rounded to acute apex, truncate base, most typically an average of 5 mm in length and 4 mm in width, surface is glabrous and dull on both surfaces, color of upper and lower surface is a blend of 76B and 75B and 145D.

*Sepals* (*pistillate flowers*).—An average of 4, obovate to oblong in shape, entire margin, rounded apex, truncate base, average of 2 mm in length and 1.2 mm in width, surface is hairy on both surfaces, color of upper and lower surface is 145C.

*Sepals* (*sterile flowers*).—Large double flowers (alkaline conditions); an average of 14, elliptic to ovate in shape, range from 8 mm to 2.5 cm in length and 5 mm to 2 cm in width (larger sepals in outer whorl), broadly acute apex, cuneate base, glabrous surface on upper and lower surface, entire margins, color of both surfaces; NN155A, changes to centers of 75B with margins NN155A, become speckled with 145B to 145C as they age with outside whorl changing first, smaller center double flowers (alkaline conditions); average of 9, elliptic to ovate in shape, range from 4 mm to 1 cm in length and 3 mm to 8 mm in width (larger sepals in outer whorl), broadly acute apex, cuneate base, glabrous surface on upper and lower surface, entire margins, color of both surfaces; open NN155A flushed with 145D, becomes marked and flushed with 75A to 75B, particularly near centers but less distinct then the larger flowers, becomes flushed with 145B to 145C as they age, under acidic conditions (small and large double flowers, both surfaces); color opens NN155A, changing to a blend of 75A to 75B and 97A and 97B with the blue coloration (97A to 97B) almost solid on the inner sepals.

*Eye* (*double flowers*).—Alkaline conditions; ranges from 145C to NN 155A to 75A to 75C, acidic conditions; 97A to 97B.

Reproductive organs: (Pistillate flowers)

*Stamens.*—None observed, astemonous with an occasional petaloid stamen.

*Pistil.*—1, average of 3 mm in length and 2 mm in width, typically 4 stigma/styles, stigma is club-shaped, 76C to 84B in color and 1 mm in diameter, style is an average of 2 mm in length and blend of 84B and 145D in color, ovary is half inferior and about 145D in color.

*Fruit and seed.*—Has not been observed under the conditions tested to date.

It is claimed:

1. A new and distinct cultivar of *Hydrangea* plant named 'Kompeito' substantially as herein illustrated and described.

* * * * *